United States Patent
Ray et al.

(10) Patent No.: US 9,265,731 B2
(45) Date of Patent: Feb. 23, 2016

(54) DRYING OF DRUG-CONTAINING PARTICLES

(75) Inventors: Roderick Jack Ray, Bend, OR (US); David Dixon Newbold, Bend, OR (US); Ronald Arthur Beyerinck, Bend, OR (US); Daniel Elmont Dobry, Bend, OR (US); Kevin Douglas Grove, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1073 days.

(21) Appl. No.: 11/814,592

(22) PCT Filed: Jan. 16, 2006

(86) PCT No.: PCT/IB2006/000186
§ 371 (c)(1), (2), (4) Date: Sep. 6, 2007

(87) PCT Pub. No.: WO2006/079921
PCT Pub. Date: Aug. 3, 2006

(65) Prior Publication Data
US 2008/0213375 A1    Sep. 4, 2008

Related U.S. Application Data

(60) Provisional application No. 60/648,229, filed on Jan. 28, 2005.

(51) Int. Cl.
*A61K 9/14* (2006.01)
*A61K 31/4706* (2006.01)
*A61K 9/16* (2006.01)

(52) U.S. Cl.
CPC .................................. *A61K 9/1694* (2013.01)

(58) Field of Classification Search
CPC .......................................................... A61K 9/16
See application file for complete search history.

(56) References Cited

U.S. PATENT DOCUMENTS

| | | | |
|---|---|---|---|
| 3,889,388 A * | 6/1975 | Oguri et al. | 34/368 |
| 4,170,074 A | 10/1979 | Heckman et al. | |
| 6,572,893 B2 * | 6/2003 | Gordon et al. | 424/489 |
| 2001/0053791 A1 * | 12/2001 | Babcock et al. | 514/419 |
| 2003/0037459 A1 * | 2/2003 | Chickering et al. | 34/576 |
| 2003/0198674 A1 * | 10/2003 | Curatolo et al. | 424/468 |
| 2003/0215515 A1 | 11/2003 | Truong-Le et al. | 424/489 |
| 2008/0213375 A1 | 9/2008 | Ray et al. | |
| 2010/0028440 A1 | 2/2010 | Dobry et al. | |

FOREIGN PATENT DOCUMENTS

| | | | |
|---|---|---|---|
| CA | 2560984 A1 | 12/2005 | |
| EP | 1027887 | 8/2000 | ............... A61K 9/26 |
| EP | 1027887 A2 * | 8/2000 | |
| WO | 03/063821 A2 | 8/2003 | |
| WO | WO 03063821 | 8/2003 | ............... A61K 9/00 |
| WO | WO2004/014342 | 2/2004 | |
| WO | WO2005/053651 | 6/2005 | |

OTHER PUBLICATIONS

Jones, David M., Fluidized Bed Processing and Drying, Pharmaceutical Engineering, Mar. 1991, 8 pages.
GEA Process Engineering, Basics of Spray Drying, http://www.niroinc.com/technologies/basics_of spray _drying.asp, 4 pages. (printed May 13, 2014).
International Search Report for PCT/IB2007/001994 (Sep. 25, 2007).
Office Action from the European Patent Office for European Patent Application No. 06700863.1 (mailed Jun. 23, 2015).

* cited by examiner

*Primary Examiner* — Robert A Wax
*Assistant Examiner* — William Craigo
(74) *Attorney, Agent, or Firm* — Klarquist Sparkman, LLP (57) ABSTRACT

A secondary drying process is disclosed for removing residual solvent from drug-containing particles that have been formed by solvent-based processes, the secondary drying process utilizing a combination of vacuum, agitation, and a stripping gas.

10 Claims, 1 Drawing Sheet

DRYING OF DRUG-CONTAINING PARTICLES

BACKGROUND OF THE INVENTION

Processes that utilize a liquid or solvent are routinely used in the preparation of solid pharmaceutical compositions. Recently it has been discovered that some pharmaceutical compositions made by a spray-drying process can enhance the aqueous concentration and bioavailability of low-solubility drugs. For example, EP 0 901 786 A2 to Curatolo et al. discloses forming solid amorphous dispersions of low solubility drugs and the polymer hydroxypropyl methyl cellulose acetate succinate by spray-drying. WO 03/000238 A1 to Babcock et al. discloses forming adsorbates of a low-solubility drug onto high surface area substrates using a spray-drying process. Such dispersions and adsorbates, which contain non-crystalline drug, provide concentration enhancement of the drug relative to crystalline drug alone.

Following formation in a spray-drying apparatus, such solid amorphous dispersions and adsorbates typically have a residual solvent content of no more than about 10 wt % and often no more than about 5 wt %. Since a desirable residual solvent content in such drug-containing particles is on the order of 1 wt % or less for purposes of drug stability and purity, secondary drying following spray drying is often required to achieve such a low residual solvent content. Another characteristic of such materials formed by spray drying is that they tend to be small (less than 500 μm) and have low-density (specific volume greater than about 1.5 cc/g).

Various dryers have been suggested for removing the residual solvent from pharmaceutical compositions, including tray dryers, fluidized-bed dryers, microwave dryers, belt dryers, and rotary dryers. See WO 01/68092 A2 and WO 03/000238 A1. However, while such secondary dryers can be effective and are commercially available, all have drawbacks. For example, tray dryers require a substantial amount of time to remove the residual solvent to the required levels and are prone to non uniformity of dried product. Fluidized-bed dryers produce a gas stream that is very dilute in the solvent, making solvent recovery inefficient, and often give relatively low product yields, particularly when the materials to be dried are very small, low-density particles. Such low-density particles are difficult to dry efficiently in a fluid bed, since the particles may become entrained in the drying gas and become trapped in the drying gas outlet filter. This leads to low product yields. Rotary dryers, which consist of a rotating drying chamber, are typically used for drying small amounts of material and require a substantial amount of time to remove the residual solvent to the required levels.

Thus, there is a need in the art for a relatively quick, energy-efficient and safe secondary drying process for producing drug-containing particles with low residual solvent concentrations.

BRIEF SUMMARY OF THE INVENTION

In one aspect, the present invention provides a process for producing a pharmaceutical composition, the process comprising the steps: (a) forming a solution comprising a drug, an excipient and a solvent; (b) atomizing the solution into droplets and removing at least a portion of the solvent from the droplets so as to form at least partially non-crystalline drug-containing particles, wherein the drug-containing particles contain less than about 10 wt % of the solvent; and (c) drying the drug-containing particles by
(i) introducing the drug-containing particles into a drying chamber having an external wall;
(ii) circulating the drug-containing particles within the drying chamber by means of a mechanical agitator independent of the wall; and
(iii) flowing a stripping gas through the drying chamber; and
(iv) removing the stripping gas and at least a portion of the solvent from the drying chamber.

In another aspect, the present invention provides a process for producing a pharmaceutical composition, the process comprising the steps: (a) forming a solution comprising a drug, an excipient and a solvent; (b) atomizing the solution into droplets and removing at least a portion of the solvent from the droplets so as to form at least partially non-crystalline drug-containing particles, wherein the drug-containing particles contain less than about 10 wt % of the solvent; and (c) drying the drug-containing particles by
(i) introducing the drug-containing particles into a drying chamber having an external wall;
(ii) circulating the drug-containing particles within the drying chamber;
(iii) flowing a stripping gas through the drying chamber and simultaneously maintaining a total pressure within said drying chamber that is less than about 0.75 atm; and
(iv) removing the stripping gas and at least a portion of the solvent from the drying chamber;
wherein step (ii) of circulating the particles comprises flowing the stripping gas through a bed of the particles.

In one embodiment, the secondary drying process removes at least 50 wt % of the solvent originally present in the particles. In another embodiment, the amount of solvent remaining in the particles following the secondary drying process is less than about 0.1 wt % of the total mass of the particles.

The invention provides one or more of the following advantages. The secondary drying process used to remove solvent from drug-containing particles facilitates mass transfer of the solvent, allowing the solvent to be removed from the particles in a timely and cost-effective manner. The process results in high yields of the dried particles, thereby minimizing processing losses. The process also allows for efficient recovery of solvent. Furthermore, because the process is conducted entirely within a closed vessel, it prevents worker exposure to the fine particles and solvent associated with the drying process and permits pneumatic transfer of the particles into and out of the drying vessel.

The foregoing and other objectives, features, and advantages of the invention will be more readily understood upon consideration of the following detailed description of the invention.

DETAILED DESCRIPTION OF PREFERRED EMBODIMENTS

Pharmaceutical compositions made by solvent processing typically contain low levels of solvent, referred to herein as "residual solvent." A large fraction of this residual solvent must typically be removed prior to the formation of dosage forms suitable for administration to a patient. The process used to remove this residual solvent is referred to herein as a "secondary drying" process. To be practical for production of pharmaceutical compositions, the secondary drying process should have the following characteristics: (1) the process must be compatible with good manufacturing practices to ensure product safety and to meet the requirements of regulatory agencies; (2) it should be relatively easy to introduce and remove the composition from the equipment used in the secondary drying process; (3) the process should be able to dry the composition to the desired residual solvent content in 20 hours or less, thereby matching the process time for typical batch processes; (4) the process should result in high product recovery; and (5) the process should produce a low volume gas stream that has a high concentration of solvent so that inexpensive and efficient solvent-recovery/removal processes can be employed. The secondary drying process described herein has these characteristics.

Secondary drying processes for drying the pharmaceutical compositions, suitable drugs and compositions are described in detail below.

Secondary Drying Process

The secondary drying process for pharmaceutical compositions made via solvent-based processes in which at least a portion of the composition is non-crystalline is unusual among drying applications for two reasons: (1) the material charged to the dryer is already in a relatively dry state; and (2) the compositions contain non-crystalline material. Many conventional drying processes start with a much higher residual solvent concentration in the material to be dried. In such conventional drying processes, the rate at which residual solvent is removed from the particles is initially limited by the rate at which heat is transferred into the particles to maintain a high enough particle temperature that evaporation of the solvent from the particle continues to be rapid. Since the heat transfer rate into the particles is typically constant for a given piece of equipment, the drying rate—that is, the rate at which residual solvent is removed from the particles—is also relatively constant until the residual solvent content begins to drop below about 5 to 10 wt % of the particle. Since the bulk of the residual solvent for conventional drying operations is removed by this process, conventional secondary drying equipment is designed to maximize the rate of heat transfer into the particles.

However, as more of the residual solvent is removed from the particles, the drying rate begins to slow. Without wishing to be bound by theory, the inventors believe that several factors contribute to the reduced rate of drying. First, the non-crystalline nature of the material to be dried may affect the drying rate. As solvent is removed from the non-crystalline material, the glass transition temperature of the material increases. This slows the rate at which solvent can diffuse from the interior to the surface of the non-crystalline material. Thus, the slow rate at which solvent can diffuse out of the particle can become the rate-limiting step for drying. Second, for tray dryers or other types of dryers in which the particles are stationary during drying, the particles are not uniformly dried, but instead dry at different rates depending on the location of the particles in the dryer. In a tray dryer, for example, particles at the bottom of the bed of particles dry more slowly than particles near the top. In order for the particles at the bottom to dry, solvent must diffuse out of the particles at the bottom, and then diffuse through the overlying bed of particles before reaching the headspace above the particles. In a rotary evaporation dryer, the wall of the drying chamber rotates, but there is no other mechanism inside the drying chamber for agitation of the particles apart from the rotating wall. When the solvent content is high, the particles tend to form agglomerates that can stick to the rotating wall surface or remain as large agglomerates. This leads to inefficient circulation of the particles in the drying chamber, resulting in a long diffusion path for the solvent to be removed.

As the solvent level in the particles becomes low for non-crystalline materials, heat transfer no longer is the rate-limiting step for removal of solvent from the particles. Rather, the rate at which the residual solvent can diffuse out of the particles and out of the bed becomes rate-limiting. In other words, for long secondary drying periods, mass transfer, rather than heat transfer, determines the drying rate for the particles. Thus, for removal of residual solvent from such solvent-based pharmaceutical compositions, it is essential that the process is designed to have good mass-transfer characteristics to ensure efficient drying of the composition in a timely manner. Specifically, the inventors have found that the partial pressure of solvent vapor at the surface of all the particles must be maintained as low as is practical.

The inventors overcame the difficulties attendant to conventional dryers by facilitating mass transfer of the solvent from the particles, rather than heat transfer. Mass transfer is facilitated by (1) exposing the particles to a controlled drying environment of low partial pressure of the solvent and (2) circulating the particles within the dryer so as to expose each of the particles to the controlled environment.

A controlled drying environment of low partial pressure of the solvent in direct contact with the surface of the particles is required in order to provide a driving force for the removal of solvent from the particles. The partial pressure of the solvent in the controlled environment in direct contact with the particle surface should be less than the partial pressure of the solvent at equilibrium with the particle. At the end of the drying process, the controlled environment has a partial pressure of the solvent that is less than the partial pressure of the solvent at equilibrium with the particle having a residual solvent content at the target dryness. For example, if the target residual solvent content for the particle is 1 wt %, and the partial pressure of the solvent in equilibrium with the particle having a solvent content of 1 wt % is 0.002 atm, then the controlled environment at the end of the drying process should have a partial pressure of the solvent that is less than 0.002 atm. The partial pressure must always be lower than the equilibrium partial pressure in the particle at any given time for mass transfer to take place. However, at the beginning of the drying process the partial pressure in the controlled environment can and often is much higher than the target partial pressure at the end of the drying process. Preferably the partial pressure of solvent within the drying chamber at the end of the drying process is less than 90% relative to the partial pressure of the solvent in equilibrium with the particles at the target solvent content, and more preferably less than 80%.

The low partial pressure of the solvent in the controlled environment may be obtained (1) by reducing the total pressure within the drying chamber, (2) by flowing a stripping gas through the drying chamber, or (3) by a combination of (1) and (2). Since the partial pressure of the solvent in the controlled atmosphere decreases with decreasing total pressure, the utility of the invention generally increases with decreasing total pressure. The pressure within the drying chamber may be less than about 0.75 atm, preferably less than about 0.5 atm, or even less than about 0.1 atm. The inventors have found operation at from about 0.01 to about 0.05 atm to be effective for most applications. In general it may be stated that the lower the total pressure is in the drying chamber, the greater is the driving force for removal of solvent from the particles. However, extremely low pressures in the drying chamber require large energy-consuming vacuum pumps. Accordingly, operation at pressures of less than about 0.01 atm is generally not energy-efficient.

When a combination of a reduced total pressure in the drying chamber and a stripping gas are used to reduce the partial pressure of solvent in the controlled environment, a reduced total pressure provides several advantages. Reducing the total pressure reduces the amount of stripping gas needed to achieve the same partial pressure of solvent. Thus, the same driving force may be obtained for removal of solvent with less stripping gas. Second, the solvent concentration in the gas exiting the dryer is higher, which may facilitate collection or disposal of the solvent.

Reducing the total pressure in the controlled environment also facilitates drying by minimizing entrainment of the particles in the stripping gas. The small, low-density particles to be dried are easily fluidized. These particles can be easily entrained by large volumes of stripping gas and transported to the stripping gas outlet filter. Reducing the total pressure in the controlled environment reduces the stripping gas flow and, in turn, the entrainment of the particles, and thus reduces the outlet filter duty cycle.

The stripping gas may be virtually any gas, but for safety reasons, and to minimize undesirable oxidation of the drug or optional excipients in the particles, an inert gas such as nitrogen, nitrogen-enriched air, or argon is typically utilized. The stripping gas is generally introduced into the drying chamber at a pressure that is less than about 8 atm, and may be less than about 5 atm, or even less than about 2 atm. When a combination of a reduced total pressure in the drying chamber and a stripping gas are used to reduce the partial pressure of solvent in the controlled environment, the stripping gas may be introduced into the drying chamber at a pressure that is less than about 1 atm. The stripping gas must be dry when introduced to the drying vessel in the sense of having little or no solvent content therein, such that the resulting partial pressure of solvent in the controlled environment is below the partial pressure required for drying. At a minimum the partial pressure of solvent in the stripping gas must be less than that of the gas stream exiting the dryer and preferably is at a partial pressure that is less than 50% of that of the exiting gas stream. The inventors have found that stripping gas flow rates of at least about 0.1 standard liters per minute per kilogram of particles to be dried (SL/min-kg) are generally effective for most applications at total pressures ranging from about 0.01 atm to about 0.1 atm. Preferably the stripping gas flow rate is at least about 0.2 SL/min-kg, and more preferably at least about 0.3 SL/min-kg. However, high stripping gas flow rates increase the operating cost of the process and can increase the stripping gas outlet filter size required to separate the particles from the stripping gas. Therefore, the stripping gas flow rate should generally be no more than about 5 SL/min-kg.

The use of a stripping gas in combination with a reduced total pressure has the advantage of allowing operation at relatively higher total pressures relative to drying by vacuum only. In general, it is difficult for conventional vacuum dryers to achieve total pressures of less than about 0.01 atm. If the partial pressure of the solvent in equilibrium with the particle at the desired residual solvent content is less than about 0.01 atm, then a conventional vacuum dryer will not be capable of drying the particles to the desired solvent content. However, the use of a stripping gas allows the total pressure to be greater than 0.01 atm, while still achieving a partial pressure of the solvent of less than 0.01 atm.

Finally, the particles in the drying chamber are circulated throughout the interior of the chamber by means of an agitator. Such circulation is necessary in order to expose all, or at least a substantial portion, of the individual particles to an environment of low partial pressure of solvent. When the bed of particles is unstirred, only the particles at the surface of the bed are actually exposed to a drying environment (low partial pressure of solvent) that approaches that in the head space of the drying chamber. This is because solvent vapor is constantly leaving the particles during drying and raising the solvent content (solvent vapor pressure) in the gas that is adjacent to the particle. In an unstirred bed, this requires that the solvent diffuse from the lower part of the bed to the surface of the bed to enter the head space. Thus, even when the solvent vapor pressure in the dryer head space is low, particles in an unagitated bed will experience a much higher solvent vapor pressure than that in the head space. The vapor pressure of solvent experienced by each particle increases (and therefore the driving force for drying decreases) as:

(1) the distance the particle is away from the surface of the bed increases; and (2) the time the particle is exposed to the surface decreases. Thus, in order for the particles to dry efficiently, it is critical that the bed of particles within the dryer not be left stagnant.

Specifically, the inventors have found that the particles can be exposed to a drying environment that more closely approaches that of the head space by:

(1) circulating the particles within the dryer by continuously or periodically moving the particles from the bed into the head space of the dryer;

(2) circulating the particles within the dryer by continuously or periodically moving the particles from the lower part of the bed to the upper surface or near the upper surface of the bed such that over time, the average distance of a particle from the upper bed surface is much less than half the average overall stagnant depth of the bed; and/or (3) circulating the particles within the drying chamber while simultaneously convectively flowing the stripping gas through the bed of particles.

Often the efficient drying processes will combine two or more of these approaches.

Figure 1:
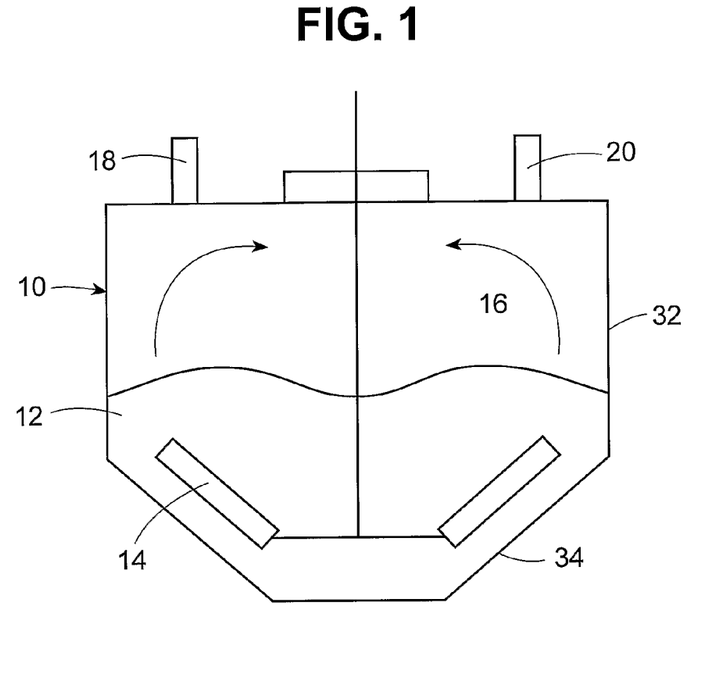
FIG. 1 is a cross-sectional schematic of an exemplary secondary drying apparatus suitable for use in the process of the invention.

The agitator should be capable of stirring or mixing the particles in the bed while causing the particles to circulate within the drying chamber so as to be moved into or close to the headspace and/or mixed with the stripping gas. The agitation should be of sufficient force to break up clumps of particles, and therefore the agitator should be independent of the external walls of the drying chamber. For example, the agitator may be a mechanical agitator, such as stir paddles, baffles attached to a rotating drum, a belt, a rotating auger or any other mechanical device capable of causing the particles to move within the drying apparatus. FIG. 1 shows schematically in cross section a drying chamber 10 having an upper cylindrical portion 32 connected to a lower conical portion 34, the cone angle ranging from about 60° to about 120°. The drying chamber contains particles 12 and a rotating stir paddle 14 to circulate the particles within the drying chamber into contact with the head space 16. Stripping gas enters the drying chamber 10 through inlet port 18 and exits through outlet port 20, which is connected to a vacuum pump (not shown) to remove stripping gas and solvent. The particles should be agitated with sufficient energy that (1) the particles are flung into the head space; (2) there is frequent contact of the particles with the head space by providing a rapid renewal of particles at the interface with the head space; or (3) a combination of (1) and (2). For example, the arrows in FIG. 1 show the particles being flung into the head space as a result of rapid rotation of the stir paddles. In a preferred embodiment, the mechanical agitation results in good contact of the particles with both the stripping gas and the head space.

One measure of the degree of mixing provided by a rotating agitator in a drying chamber is the Froude number. The Froude number is a dimensionless parameter defined as the ratio of inertial force to gravitation force, and is characterized as follows:

$$Fr=[V^2/gD]=\text{Froude Number}$$

where V is the characteristic velocity of the particles in the drying chamber, D is the characteristic diameter, and g is the acceleration due to gravity. For a rotating agitator such as an impeller, the characteristic velocity may be defined as $V=\pi DN$, where D is the diameter of the agitator and N is the impeller rotation in revolutions per unit time. In this case, the Froude number may be rewritten as $[(\pi DN)^2/gD]$. Good mixing of the particles in a drying chamber of the configuration shown schematically in FIG. 1 may be achieved where the Froude number is at least about 0.01, more preferably at least about 0.1, and even more preferably at least about 0.2.

Figure 2:
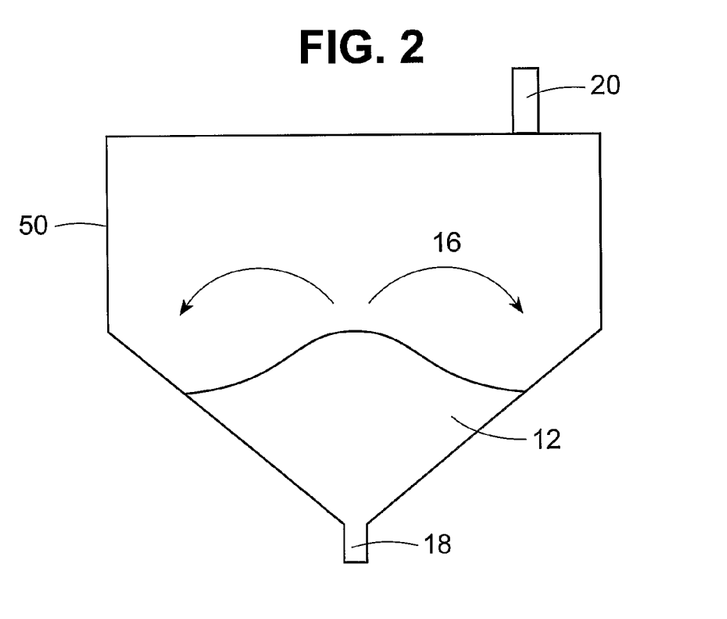
FIG. 2 is a cross-sectional schematic of an alternative exemplary secondary drying apparatus suitable for use in the process of the invention.

Alternatively, the agitator may consist of a device capable of blowing the stripping gas into the bed of particles so as to cause the particles to circulate within the drying chamber. Specifically, when the stripping gas is introduced at the bottom of the bed of particles at a high flow rate, the bed of particles may be in a bubbling or turbulent regime, circulating the particles continuously into the head space of the dryer and exposing them to the low solvent vapor pressure of the dryer head space. However, care must be taken that the particles do not become so fluidized that the particles become entrained in the stripping gas. Thus, it is often desirable to flow the stripping gas through the particle bed at a slower rate such that particles are only periodically thrown into the dryer head space. For example, FIG. 2 shows an alternative drying chamber 50 in which the inlet port 18 is located at the bottom of the chamber to cause the particles to circulate up into contact with the head space 16. Since the particles are very small and have low-density, it is also desired to minimize entrainment of the particles in the stripping gas for those embodiments that utilize a stripping gas. This may be accomplished through a variety of techniques. For example, as described above, the total pressure within the drying apparatus may be kept low. This allows the volume of stripping gas to be reduced while still having rapid drying. This reduces entrainment of the particles.

As yet another alternative, the particles may be circulated using a combination of the stripping gas flow and mechanical agitation.

Circulating the particles within the drying chamber to expose substantially all of the particles periodically to the controlled environment of low partial pressure of the solvent facilitates mass transfer of solvent by exposing all, or at least a significant fraction, of the particles for at least some period of time to the controlled environment in or near the headspace, the stripping gas, or both. This allows solvent to diffuse directly out of each of the particles for at least some period of time and into the controlled environment, such as the headspace, without the need to diffuse through an overlying bed of particles. When circulated, the particles achieve good contact with the stripping gas and/or with the upper surface of the bed near the head space in the drying chamber. This results in fast mass transfer of residual solvent into the stripping gas and head space; the solvent vapor in the stripping gas is then removed from the drying chamber through the outlet port by means of the vacuum pump. This is in contrast to a conventional fluidization drying process that uses large volumes of drying gas flowing up through and suspending the mass of particles. Instead, in the process of the present invention, the goal is to circulate the particles sufficiently to achieve good contact between the particles and both the stripping gas and the controlled drying environment, such as the upper surface near the head space of the drying vessel, without the need to simultaneously suspend the particles in the flowing gas. Thus, unlike a fluid bed dryer, the flow rate of the stripping gas may be controlled without the need to suspend the particles in the stripping gas.

As a result of the circulation of particles within the drying chamber, the present invention has increasing utility as the bed depth of particles increases. Thus, the process improves drying efficiency for an average bed depth that is at least about 10 cm, at least about 20 cm, at least about 30 cm, or even at least about 50 cm. An average bed depth may be determined by taking the average distance between the bed surface and the bottom of the drying chamber for an unstirred bed.

The secondary drying process may also be performed at elevated temperatures to increase the vapor pressure of the solvent and, in turn the driving force for removal of solvent from the particles. This may be accomplished by heating the drying chamber or by heating the stripping gas introduced into the drying chamber, or both. The drying chamber may be heated, for example, by circulating a heating fluid in a jacket surrounding the dryer. Preferred heating temperatures range from about 35° C. to about 60° C. or higher, depending upon the nature and solvent content of the particles to be dried.

At least a portion of the solvent in the particles is removed from the drying chamber during the secondary drying process of the invention. By "at least a portion" means that upon completion of the secondary drying process of the invention, the amount of solvent removed from the particles is at least about 50 wt % as compared to the amount of solvent in the particles upon commencement of the secondary drying process, preferably at least about 80 wt %, more preferably at least about 90 wt % and most preferably at least about 95 wt %. In absolute terms, the amount of solvent remaining in the particles is less than about 1 wt % of the total mass of the particles, preferably less than about 0.5 wt %, and most preferably less than about 0.1 wt %.

The drying process may be conducted in any device capable of (1) exposing the particles to a controlled environment of low partial pressure of the solvent and (2) circulating the particles within the dryer so as to repeatedly move the particles to a position near the upper surface of the particle bed near the head space. This circulation results in the particles being exposed to a relatively low solvent partial pressure near or equivalent to that of the controlled drying environment in the head space. For example, the drying chamber may be similar to the configuration shown in FIG. 1. Alternatively, the drying chamber may be a tray dryer in which the trays contain stir paddles to circulate the particles. As another example, the drying chamber may contain a rotating drum with baffles to circulate the particles. As yet another example, the drying chamber may contain a series of horizontal plates and a rotating shaft with arms and plows that convey the particles from one plate to another. As yet another example, in a Turbo tray dryer consisting of a stack of rotating trays, the material is wiped from one tray to the one below (Perry's *Chemical Engineer's Handbook*, 5$^{th}$ ed., 1973, Pg 20-47) or the Multi-Louvre dryer which uses a louvered conveyor which picks up material and dumps it in a thin stream over a ventilated ascending louver. (Perry's *Chemical Engineer's*

Handbook, 5*th* ed., 1973, Pg 20-53). The drying chamber is preferably made out of stainless steel and is stationary during operation (that is, the drying chamber does not rotate or move during operation of the dryer).

As described herein below, the particles to be dried are typically small and have a low density. Therefore, the drying chamber may be equipped with pneumatic transfer tubes for pneumatically transferring both the particles to be dried and the dried particles into and out of, respectively, the drying chamber. Such pneumatic transfer may be utilized to reduce or eliminate exposure of workers to the particles and to the residual solvent. Pneumatic transfer may also be used to reduce contact of the drug in the drug-containing particles with air, thereby preventing possible oxidation and/or degradation of the drug.

The particles are typically dried in a batch process by charging the drying chamber with the particles to be dried via either the stripping gas inlet port or another port. The stripping gas may be introduced near the bottom of the drying chamber, near the middle or even in the headspace. Once dried, the drug-containing particles may be discharged via an outlet, such as a port located at the bottom of the drying chamber. The stripping gas outlet port may be provided with a back-pulse filter in fluid communication with a vacuum pump.

Solvent-Based Processes

The secondary drying process of the present invention is suitable for removing residual solvent from drug-containing particles formed by solvent-based processes in which at least a portion of the drug-containing particles is in a non-crystalline state. As used herein, the term "crystalline" refers to solid material in which atoms or molecules are arranged in a definite pattern that is repeated regularly in three dimensions. The term "non-crystalline" refers to solid material that is not crystalline, and therefore does not have long-range three dimensional translational order. Material in a non-crystalline state is sometimes referred to in the art as being in an amorphous state. The term "non-crystalline" is intended to include not only material which has essentially no order, but also material which may have some small degree of order, but the order is in less than three dimensions and/or is only over short distances. Partially crystalline materials, liquid crystals, and disordered crystals are included as well. Non-crystalline material may be characterized by techniques known in the art such as powder x-ray diffraction (PXRD) crystallography, solid state NMR, or thermal techniques such as differential scanning calorimetry (DSC). For example, when evaluated by PXRD, non-crystalline material exhibits a deviation from a flat baseline, referred to in the art as an amorphous halo. In another example, when evaluated by DSC, non-crystalline material will exhibit a glass-transition temperature ($T_g$).

At least a portion of the drug-containing particles is in a non-crystalline state. By "at least a portion" is meant that at least about 10 wt % of the material in the particles is in a non-crystalline or amorphous state. The process of the present invention finds greater utility as the percentage of the non-crystalline material in the particles increases. Thus, the amount of non-crystalline material present in the particles may be at least about 25 wt %, at least about 50 wt %, at least about 75 wt %, or even at least about 95 wt %. In one embodiment essentially all of the material in the particles is non-crystalline, meaning that no crystalline material is present in the particle within the detection limits of suitable analytical techniques.

In one embodiment, the particles consist essentially of drug, at least a portion of which is non-crystalline. In another embodiment, the particles comprise a drug and at least one excipient, wherein at least a portion of the drug, a portion of the excipient, or a portion of both are in a non-crystalline state. In yet another embodiment, the particles comprise a drug and at least one polymer, wherein at least a portion of the drug, at least a portion of the polymer, or a portion of both are in a non-crystalline state.

The drug-containing particles are formed by a solvent-based process. By "solvent-based process" and "solvent process" are meant that the process used to form the drug-containing particles makes use of a solvent. In solvent processes, the drug and optional excipients may be dissolved in the solvent, suspended in the solvent, wetted by the solvent, or any combination of these. The solvent-based process then forms drug-containing particles comprising the drug, optional excipients, and residual solvent. The solvent-based process may involve removal of a portion of the solvent from the particles. In any event, the resulting drug-containing particles also contain residual solvent. Exemplary solvent-based processes include wet granulation, extrusion-spheronization, wet milling, spray-coating, and spray-drying.

Solvents suitable for solvent processing are preferably volatile with a boiling point of 150° C. or less. In addition, the solvent should have relatively low toxicity and be pharmaceutically acceptable. Preferred solvents include water; alcohols such as methanol, ethanol, the various isomers of propanol, the various isomers of butanol, 1-pentanol, and 2-methyl-1-propanol; organic acids, such as acetic acid and formic acid; ketones such as acetone, methyl ethyl ketone, methyl iso-butyl ketone, cyclohexanone; esters, such as methyl acetate, ethyl formate, ethyl acetate, propyl acetate, and butyl acetate; ethers, such as dimethyl ether, ethyl ether, tert-butyl-methyl ether, 1,2, dimethoxyethane, 2-ethoxyethanol, 2-methoxyethanol, tetrahydrofuran, methyl tetrahydrofuran, 1,3-dioxolane, and 1,4-dioxane; alkanes, such as butane, pentane, hexane, heptane, cyclohexane, and methylcyclohexane; alkenes, such as pentene, hexene, and cyclohexene; nitriles, such as acetonitrile; alkyl halides, such as methylene chloride, chloroform, dichloroethane, dichloroethene, trichloroethane, and trichloroethylene; aromatics, such as benzene, toluene, xylene, ethylbenzene, anisole, cumene, and chlorobenzene; pyridine; and mixtures thereof. Lower volatility solvents such as dimethyl acetamide or dimethylsulfoxide can also be used in small amounts in mixtures with a volatile solvent. Mixtures of solvents, such as 50% methanol and 50% acetone, can also be used, as can mixtures with water. Preferred solvents include acetone, methyl ethyl ketone, methyl isobutyl ketone, methanol, ethanol, the various isomers of propanol, methyl acetate, ethyl acetate, toluene, methylene chloride, tetrahydrofuran, 1,4-dioxane, 1,3-dioxolane, and mixtures thereof. Most preferred solvents include acetone, methanol, ethanol, the various isomers of propanol, ethyl acetate, and mixtures thereof. Mixtures of the above with water may also be used.

The drug-containing particles may be formed by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50

Chem. Eng. Prog. Monogr. Series 2 (1954), and Masters, Spray Drying Handbook (Fourth Edition 1985), the disclosure of which is incorporated herein by reference.

Various types of nozzles can be used to atomize the spray solution, thereby introducing the spray solution into the spray-dry apparatus as a collection of small droplets. Essentially any type of nozzle may be used to spray the solution as long as the droplets that are formed are sufficiently small that they dry sufficiently (due to evaporation of solvent) that they do not stick to or coat the spray-drying apparatus wall.

Although the maximum droplet size varies widely as a function of the size, shape and flow pattern within the spray-dryer, generally droplets should be less than about 500 μm in diameter when they exit the nozzle. Examples of types of nozzles that may be used to form the particles include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. application Ser. No. 10/351,568, the disclosure of which is incorporated herein by reference.

Particles formed in a spray drying process typically have a mean size of less than about 500 μm in diameter, and may be less than about 100 μm in diameter, less than about 50 μm in diameter or even less than about 25 μm in diameter. The particles are also typically of low density, having a bulk specific volume of at least about 1.5 mL/g, and typically at least about 2 mL/g.

In a typical spray-drying process, the final solvent content of the particles as they leave the spray-drying chamber is less than about 10 wt % and often less than about 5 wt %. However, it is generally not practical or economical to operate a spray dryer to obtain particles having a solvent content of less than about 1 wt %. Following formation, the particles are dried in the secondary drying process of the present invention.

The drug-containing particles may also be formed by spraying the solvent-bearing feed solution onto seed cores. The seed cores can be made from any suitable material such as starch, microcrystalline cellulose, sugar or wax, by any known method, such as melt- or spray-congealing, extrusion/spheronization, granulation, spray-drying and the like. The feed solution can be sprayed onto such seed cores using coating equipment known in the pharmaceutical arts, such as pan coaters (e.g., Hi-Coater available from Freund Corp. of Tokyo, Japan, Accela-Cota available from Manesty of Liverpool, U.K.), fluidized bed coaters (e.g., Würster coaters or top-sprayers available from Glatt Air Technologies of Ramsey, N.J. and from Niro Pharma Systems of Bubendorf, Switzerland) and rotary granulators (e.g., CF-Granulator, available from Freund Corp). During this process, the seed cores are coated with the feed solution and the solvent is evaporated, resulting in a coating comprising the drug, optional excipients, and residual solvent. The resulting particles are then dried in the secondary drying process of the present invention.

Particles formed by spraying the solvent-bearing feed solution onto seed cores typically have a mean size after coating of less than about 1000 μm in diameter, and may be less than about 500 μm in diameter, less than about 300 μm in diameter, or even less than about 100 μm in diameter. The particles typically have a bulk specific volume of less than about 5 mL/g, and may be less than about 3 mL/g, or even less than about 2 mL/g.

The Drug

The particles to be dried by the process of the present invention include a drug. The term "drug" is conventional, denoting a compound having beneficial prophylactic and/or therapeutic properties when administered to an animal, especially humans.

The drug may be in a crystalline, semi-crystalline, amorphous or semi-ordered state or a combination of these states or states that lie between.

The drug may be present in the particles to be dried in an amount ranging from about 1 to about 100 wt %, and most preferably from about 10 to about 80 wt %.

The present invention is particularly suitable for compositions comprising a "low-solubility drug," meaning that the drug has a minimum aqueous solubility at physiologically relevant pHs (i.e., pH 1-8) of about 0.5 mg/mL or less. The drug may have an even lower aqueous solubility, such as less than about 0.1 mg/mL, less than about 0.05 mg/mL, and even less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (i.e., solutions with pH 1-8), including USP simulated gastric and intestinal buffers, and dose is in mg. Thus, a dose-to-aqueous solubility ratio may be calculated by dividing the dose (in mg) by the aqueous solubility (in mg/mL).

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, triglyceride-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein (CETP) inhibitors.

Each named drug should be understood to include the neutral form of the drug or pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, delaverdine, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4',6'-trimethylphenoxy)pyridine, pyroxidine, fluoxetine, paroxetine, venlafaxine and sertraline; specific examples of antibiotics include carbenicillin indanyl-sodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, levocetirizine, decarboethoxyloratadine, and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; specific examples of CETP inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester (torcetrapib), [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2 tetrafluoroethoxy)phenyl]methyl]amino]-1,1,1-trifluoro-2-propanol, (2R,4R,4aS)-4-[amino-(3,5-bis-(trifluoromethyl-phenyl)-methyl]-2-ethyl-6-(trifluoromethyl)-3,4-dihydro-quinoline-1-carboxylic acid isopropyl ester, S-[2-([[1-(2-ethylbutyl)cyclohexyl]carbonyl]amino)phenyl]2-methylpropanethioate, trans-4-[[[2-[[[[3,5-bis(trifluoromethyl)phenyl]methyl](2-methyl-2H-tetrazol-5-yl)amino]methyl]-4-(trifluoromethyl)phenyl]ethylamino] methyl]-cyclohexaneacetic acid, trans-4-[[[2-[[[[3,5-bis (trifluoromethyl)phenyl]methyl](2-methyl-2H-tetrazol-5-yl)amino]methyl]-5-methyl-4-(trifluoromethyl)phenyl] ethylamino]methyl]-cyclohexaneacetic acid; the drugs disclosed in commonly owned U.S. patent application Ser. Nos. 09/918,127 and 10/066,091, the disclosures of which are incorporated herein by reference; and the drugs disclosed in the following patents and published applications: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 200018721; WO 200018723; WO 200018724; WO 200017164; WO 200017165; WO 200017166; WO 2004020393; EP 992496; and EP 987251, the disclosures of all of which are incorporated by reference.

Solid Amorphous Dispersions

One especially preferred class of drug-containing particles formed by solvent-based processes comprises solid amorphous dispersions of a drug and at least one polymer. Suitable polymers for inclusion in solid amorphous dispersions and the other types of solvent-based pharmaceutical composition particles disclosed herein are described infra. At least a major portion of the drug in the dispersion is amorphous. As used herein, the term "a major portion" of the drug means that at least 60% of the drug in the dispersion is in the amorphous, as opposed to the crystalline form. By "amorphous" is meant simply that the drug is in a non-crystalline state. Preferably, the drug in the dispersion is "substantially amorphous," meaning that the amount of the drug in crystalline form does not exceed about 25%. More preferably, the drug in the dispersion is "almost completely amorphous," meaning that the amount of drug in the crystalline form does not exceed about 10%. Amounts of crystalline drug may be measured by Powder X-Ray Diffraction (PXRD), Scanning Electron Microscope (SEM) analysis, Differential Scanning Calorimetry (DSC) or any other standard quantitative measurement.

The amount of drug relative to the amount of polymer present in the solid amorphous dispersions suitable for drying by the process of the present invention depends on the drug and the properties of the polymer and may vary widely from a drug-to-polymer weight ratio of from 0.01 to about 100 (e.g., 1 wt % drug to 99 wt % drug). In most cases it is preferred that the drug-to-polymer ratio is greater than about 0.05 (4.8 wt % drug) and less than about 20 (95 wt % drug).

The amorphous drug can exist within the solid amorphous dispersion as a pure phase, as a solid solution of drug homogeneously distributed throughout the polymer or any combination of these states or those states that lie between them. Preferably, at least a portion of the amorphous drug and polymer are present as a solid solution. This may be shown by the presence of at least one glass transition temperature for the solid amorphous dispersion that is intermediate that of the pure drug and pure polymer. In a preferred embodiment, the dispersion is substantially homogeneous so that the amorphous drug is dispersed as homogeneously as possible throughout the polymer. As used herein, "substantially homogeneous" means that the fraction of drug present in relatively pure amorphous domains within the solid dispersion is relatively small, on the order of less than 20%. Even more preferably, the dispersion is completely homogeneous, meaning the amount of drug in pure amorphous domains is less than 10% of the total amount of drug.

Solid amorphous dispersions may be made by a solvent-based process as follows. A feed solution is formed comprising the drug, a polymer, and a solvent. The solvent is then rapidly removed from the feed solution to form particles of drug and polymer. Suitable processes for rapidly removing the solvent include spray-drying, spray-coating, and evaporation. Further details of the spray-drying process for forming solid amorphous dispersions are disclosed in U.S. patent application Ser. No. 09/131,019 filed Aug. 7, 1998, which claimed priority of U.S. Provisional Patent Application Ser. No. 60/055,221 filed Aug. 11, 1997, the disclosures of which are incorporated herein by reference. Following formation, the drug-containing adsorbate particles are dried in the secondary drying process of the invention.

Semi-Ordered Drug-Containing Compositions

Another preferred class of drug-containing particles formed by solvent-based processes comprises a solid mixture of a low-solubility drug and a polymer wherein at least a portion of the drug is "semi-ordered." By "semi-ordered" is meant that (1) the drug is less ordered than drug in bulk crystalline form alone and (2) the drug has greater order than amorphous drug. The drug in the semi-ordered state may be in the form of extremely small crystals (e.g., less than about 200 nm), crystalline drug which has polymer incorporated into the crystals, crystals containing a multitude of crystal defects, or semi-crystalline structures which take the form of sheets, tubes, or other structures in which the drug is ordered but is not in the lowest solubility, bulk crystalline form alone. Drug that is semi-ordered exhibits physical characteristics that are distinct from both bulk crystalline drug and amorphous drug. That the drug is semi-ordered may be demonstrated by conventional techniques used to characterize whether a material is crystalline or amorphous. In such particles, at least a portion of the drug, a portion of the polymer, or both are in a non-crystalline state.

One method to form compositions containing semi-ordered drug is to first form a solid amorphous dispersion, as previously described. The dispersion is then exposed to a mobility-enhancing agent, such as one of the solvents previously described, and then treated to convert at least a portion of the amorphous drug in the dispersion into the semi-ordered state. Details of methods for making semi-ordered drugs and techniques for verifying that the drug is in a semi-ordered state (including PXRD, spectroscopic analysis and thermal techniques) are disclosed in U.S. patent application Ser. No. 10/636,834 filed Aug. 5, 2003, the disclosure of which is incorporated herein by reference. Following formation, the particles of polymer and drug in the semi-ordered state are dried using the secondary drying process of the invention.

Adsorbates

Another preferred class of drug-containing particles formed by solvent-based processes is an adsorbate comprising a drug and a substrate. At least a major portion of the drug in the adsorbate is amorphous in the same sense noted above in connection with the discussion of solid amorphous dispersions. Preferably, the drug in the adsorbate is substantially amorphous, more preferably almost completely amorphous and most preferably, the drug is in a completely amorphous form within the detection limits of the techniques used for characterization.

The adsorbate includes a high surface area substrate. The substrate is preferably any material that is inert, meaning that the substrate does not adversely interact with the drug to an unacceptably high degree and which is pharmaceutically acceptable. The substrate is also preferably insoluble in the solvent used in the solvent process to form the adsorbate. The substrate should have a high surface area, meaning that its surface area is at least about 20 $m^2/g$, preferably at least about 50 $m^2/g$, more preferably at least about 100 $m^2/g$, and most preferably at least about 180 $m^2/g$. The higher the surface area of the substrate, the higher the drug-to-substrate ratio that can be achieved, which leads to improved physical stability. Thus, effective substrates can have surface areas of from about 200 $m^2/g$, up to about 600 $m^2/g$ or more. The substrate should also be in the form of small particles ranging in size of from about 10 nm to about 1 μm, preferably from about 20 nm to about 100 nm. These particles may in turn form agglomerates ranging in size from about 10 nm to about 100 μm.

Solvent processes may be used to form the adsorbates as follows. The drug is first dissolved in a solvent, and then the high surface area substrate is suspended in the solution. The solvent is then rapidly removed from the solution using processes such as spray-drying. Such solvent processes useful in forming the adsorbate particles are described in detail in commonly assigned U.S. patent application Ser. No. 10/173,987, filed Jun. 17, 2002, the disclosure of which is incorporated herein by reference. Following formation, the drug-containing adsorbate particles are dried in the secondary drying process of the invention.

Polymers

In some embodiments, the pharmaceutical composition to be dried may contain a polymer. Polymers suitable for use in the various solvent-processed compositions of the present invention should be pharmaceutically acceptable, and should have at least some solubility in aqueous solution at physiologically relevant pHs (i.e., pH 1-8). Almost any neutral or ionizable polymer that has an aqueous solubility of at least 0.1 mg/mL over at least a portion of the pH 1-8 range is suitable.

In one embodiment the polymer is "amphiphilic" in nature, meaning that the polymer has hydrophobic and hydrophilic portions. It is believed that amphiphilic polymers tend to have relatively strong interactions with the drug and may promote the formation of various types of polymer/drug assemblies in solution. A particularly preferred class of amphiphilic polymers are those that are ionizable, the ionizable portions of such polymers, when ionized, constituting at least a portion of the hydrophilic portions of the polymer.

One class of polymers suitable for use with the present invention comprises neutral non-cellulosic polymers. Exemplary polymers include: vinyl polymers and copolymers having at least one substituent selected from the group comprising hydroxyl, alkylacyloxy, and cyclicamido; vinyl copolymers of at least one hydrophilic, hydroxyl-containing repeat unit and at least one hydrophobic, alkyl- or aryl-containing repeat unit; polyvinyl alcohols that have at least a portion of their repeat units in the unhydrolyzed (vinyl acetate) form; polyvinyl alcohol polyvinyl acetate copolymers; polyvinyl pyrrolidone; polyethylene polyvinyl alcohol copolymers, and polyoxyethylene-polyoxypropylene block copolymers (also referred to as poloxamers).

Another class of polymers suitable for use with the present invention comprises ionizable non-cellulosic polymers. Exemplary polymers include: carboxylic acid-functionalized vinyl polymers, such as the carboxylic acid functionalized polymethacrylates and carboxylic acid functionalized polyacrylates such as the EUDRAGITS® manufactured by Rohm Tech Inc., of Malden, Mass.; amine-functionalized polyacrylates and polymethacrylates; high molecular weight proteins such as gelatin and albumin; and carboxylic acid functionalized starches such as starch glycolate.

A preferred class of polymers comprises ionizable and neutral (or non-ionizable) cellulosic polymers with at least one ester- and/or ether-linked substituent in which the polymer has a degree of substitution of at least 0.05 for each substituent. It should be noted that in the polymer nomenclature used herein, ether-linked substituents are recited prior to "cellulose" as the moiety attached to the ether group; for example, "ethylbenzoic acid cellulose" has ethoxybenzoic acid substituents. Analogously, ester-linked substituents are recited after "cellulose" as the carboxylate; for example, "cellulose phthalate" has one carboxylic acid of each phthalate moiety ester-linked to the polymer and the other carboxylic acid unreacted.

Exemplary non-ionizable cellulosic polymers that may be used as the polymer include: hydroxypropyl methyl cellulose acetate, hydroxypropyl methyl cellulose (HPMC), hydroxypropyl cellulose, methyl cellulose, hydroxyethyl methyl cellulose, hydroxyethyl cellulose acetate, and hydroxyethyl ethyl cellulose.

Exemplary cellulosic polymers that are at least partially ionized at physiologically relevant pHs include: hydroxypropyl methyl cellulose acetate succinate (HPMCAS), hydroxypropyl methyl cellulose succinate, hydroxypropyl cellulose acetate succinate, hydroxyethyl methyl cellulose succinate, hydroxyethyl cellulose acetate succinate, hydroxypropyl methyl cellulose phthalate (HPMCP), hydroxyethyl methyl cellulose acetate succinate, hydroxyethyl methyl cellulose acetate phthalate, carboxyethyl cellulose, carboxymethyl ethylcellulose (CMEC), carboxymethyl cellulose, cellulose acetate phthalate (CAP), methyl cellulose acetate phthalate, ethyl cellulose acetate phthalate, hydroxypropyl cellulose acetate phthalate, hydroxypropyl methyl cellulose acetate phthalate, hydroxypropyl cellulose acetate phthalate succinate, hydroxypropyl methyl cellulose acetate succinate phthalate, hydroxypropyl methyl cellulose succinate phthalate, cellulose propionate phthalate, hydroxypropyl cellulose butyrate phthalate, cellulose acetate trimellitate (CAT), methyl cellulose acetate trimellitate, ethyl cellulose acetate trimellitate, hydroxypropyl cellulose acetate trimellitate, hydroxypropyl methyl cellulose acetate trimellitate, hydroxypropyl cellulose acetate trimellitate succinate, cellulose propionate trimellitate, cellulose butyrate trimellitate, cellulose acetate terephthalate, cellulose acetate isophthalate, cellulose acetate pyridinedicarboxylate, salicylic acid cellulose acetate, hydroxypropyl salicylic acid cellulose acetate, ethylbenzoic acid cellulose acetate, hydroxypropyl ethylbenzoic acid cellulose acetate, ethyl phthalic acid cellulose acetate, ethyl nicotinic acid cellulose acetate, and ethyl picolinic acid cellulose acetate. Of these cellulosic polymers that are at least partially ionized at physiologically relevant pHs, those that the inventors have found to be most preferred are HPMCAS, HPMCP, CAP, CAT, carboxyethyl cellulose, carboxymethyl cellulose, and CMEC. While specific polymers have been discussed as being suitable for use in the drug-containing particles of the present invention, blends of such polymers may also be suitable. Thus the term "polymer" is intended to include blends of polymers in addition to a single species of polymer.

Of all of the foregoing polymers, those most preferred are HPMCAS, HPMCP, HPMC, CAP, CAT, CMEC, poloxamers, and blends thereof.

EXAMPLES

Dispersion 1

A solid amorphous dispersion was formed comprising [2R, 4S]4-[(3,5-bis trifluoromethyl-benzyl)-methoxycarbonyl-amino]-2-ethyl-6-trifluoromethyl-3,4-dihydro-2H-quinoline-1-carboxylic acid ethyl ester, also known as torcetrapib (Drug 1), having the following chemical structure:

The dispersion was made by first forming a spray solution containing 4 wt % Drug 1 and 12 wt % hydroxypropyl methyl cellulose acetate succinate (HPMCAS) (AQOAT-MG available from Shin Etsu, Tokyo, Japan) in acetone. The spray solution was pumped using a Bran-Luebbe VE-D31 high-pressure pump to a spray drier (Niro type XP Portable Spray Drier with a Liquid-Feed Process Vessel Model PSD-2) equipped with a pressure nozzle (Spraying Systems SK-71-27). The spray solution was pumped to the spray drier at about 66 kg/hr, with an atomization pressure of about 800 psig (55 atm). Nitrogen drying gas entered the drying chamber at an inlet temperature of 112° C., and a flow rate of about 520 m$^3$/hr. The evaporated solvent and wet drying gas exited the spray drier at the outlet at a temperature of about 40° C. The solid amorphous dispersion formed by this process, containing 25 wt % Drug 1 and 75 wt % HPMCAS-MG, was collected in a cyclone.

The properties of the solid amorphous dispersion after spray-drying are given in Table 1. The Bulk and Tapped Specific Volumes of the dispersion were determined using the following procedures. A sample of the dispersion was poured into a 100-mL graduated cylinder, the tare weight of which had been measured, and the volume and weight of the sample recorded. The volume divided by the weight yielded the Bulk Specific Volume in mL/g. Next, the cylinder containing the dispersion was tapped 2000 times using a VanKel tap density instrument, model 50-1200. The tapped volume divided by the same weight of dispersion yielded a Tapped Specific Volume in mL/g.

The volume-weighted mean particle diameter of the solid amorphous dispersion was measured by recording data from laser light scattering using a Malvern Mastersizer 2000, then performing a calculation based on the data. A dry powder feed method was used, and samples were taken at a rate of 3 measurements per aliquot with a delay time of 7 seconds. The dispersive air pressure was 2 barg, and the vibration feed rate was 75% of maximum. Volume-weighted mean diameter was calculated from the light scattering data assuming a gaussian size distribution, with approximately 85% of the particle volume being within about 30% of the reported size.

TABLE 1

| Bulk Properties (Before Secondary Drying) | Value |
|---|---|
| Bulk Specific Volume (mL/g) | 3.9 |
| Tapped Specific Volume (mL/g) | 2.6 |
| Mean Particle Diameter (μm) | 55 |

Examples 1-10

A secondary drying apparatus was fabricated by modifying a vertical process dryer (VPT) obtained from Ekato (Schopfheim, Germany) having a 3-liter capacity and an agitator diameter of 0.2 m. The VPT dryer was modified by fitting it with dual gas inlets near the bottom of the drying chamber so that a stripping gas of dry nitrogen could be fed into the drying chamber. This apparatus was used to remove residual solvent (acetone) from solid amorphous dispersions made by the spray-drying process used to form Dispersion 1. The conditions in the secondary drying apparatus were varied to examine the effects of operating variables on performance. In each example, the drying chamber was charged with about 3 liters (600 g) of the spray-dried Dispersion 1. Hot water was circulated through the jacketed drying chamber to adjust the temperature during each experiment. The drier operating conditions for Examples 1-10 are shown in Table 2.

TABLE 2

| Example | Temp. (° C.) | Chamber Pressure (mbar) | Flow rate of Nitrogen Stripping gas SL/min* | Flow rate of Nitrogen Stripping gas SL/min-kg** | Mixing Speed (rpm) | Mixing Velocity (m/sec)*** | Froude Number |
|---|---|---|---|---|---|---|---|
| 1 | 45 | 30 | 0.2 | 0.33 | 200 | 2.1 | 2.3 |
| 2 | 55 | 10 | 0.2 | 0.33 | 200 | 2.1 | 2.3 |
| 3 | 45 | 29 | 0.6 | 1.00 | 100 | 1.0 | 0.5 |
| 4 | 50 | 21 | 0.4 | 0.67 | 150 | 1.6 | 1.3 |
| 5 | 55 | 30 | 0.2 | 0.33 | 200 | 2.1 | 2.3 |
| 6 | 55 | 30 | 0.6 | 1.00 | 200 | 2.1 | 2.3 |
| 7 | 45 | 10 | 0.2 | 0.33 | 100 | 1.0 | 0.5 |
| 8 | 50 | 20 | 0.4 | 0.67 | 150 | 1.6 | 1.3 |
| 9 | 45 | 12 | 0.6 | 1.00 | 200 | 2.1 | 2.3 |
| 10 | 55 | 14 | 0.6 | 1.00 | 100 | 1.0 | 0.5 |

*Standard Liters per minute
**Standard Liters per minute per kg of particles to be dried
***Mixing velocity = πDN, where D = 0.2 m and N = mixing speed (in rev/sec)

Samples of the spray-dried dispersion were removed from the drying chamber during each drying operation and analyzed for residual acetone by headspace gas chromatography (GC). Specifically, dispersion samples were collected at 2 minutes, then at 10-minute intervals during the first hour of drying, then at the longer intervals indicated in Table 3. For the GC analysis, a sufficient amount of the dispersion was taken at each time interval to fill a vial completely, with minimal void space. The vial was then sealed and stored at 0° C. until analysis. To analyze each sample, the sample was weighed, and dimethyl acetamide (DMAC) was added to dissolve the sample. Each sample in DMAC was injected onto a GC column and the acetone peak area was compared to standards to determine the amount of acetone in the sample of dispersion. The weight of acetone as a percentage of the total sample weight was calculated and is reported in Table 3.

TABLE 3

| Sample | Time (min) | Acetone (wt %) |
|---|---|---|
| Example 1 | 2 | 1.9 |
| | 10 | 1.2 |
| | 20 | 0.76 |
| | 30 | 0.54 |
| | 40 | 0.42 |
| | 50 | 0.33 |
| | 60 | 0.26 |
| | 90 | 0.15 |
| | 120 | 0.095 |
| | 180 | 0.044 |
| | 240 | 0.023 |
| Example 2 | 2 | 1.4 |
| | 10 | 0.57 |
| | 20 | 0.29 |
| | 30 | 0.19 |
| | 40 | 0.14 |
| | 50 | 0.11 |
| | 60 | 0.088 |
| | 90 | 0.043 |
| | 120 | 0.023 |
| | 180 | 0.009 |
| Example 3 | 2 | 1.7 |
| | 10 | 1.0 |
| | 20 | 0.75 |
| | 30 | 0.49 |
| | 40 | 0.34 |
| | 50 | 0.26 |
| | 60 | 0.2 |
| | 90 | 0.088 |
| | 120 | 0.05 |
| | 180 | 0.022 |
| Example 4 | 2 | 1.6 |
| | 10 | 1.1 |
| | 20 | 0.45 |
| | 30 | 0.28 |
| | 40 | 0.20 |
| | 50 | 0.13 |
| | 60 | 0.091 |
| | 90 | 0.044 |
| | 120 | 0.03 |
| | 180 | 0.018 |
| Example 5 | 2 | 1.5 |
| | 10 | 0.72 |
| | 20 | 0.35 |
| | 60 | 0.035 |
| | 90 | 0.019 |
| Example 6 | 2 | 1.5 |
| | 10 | 1.1 |

TABLE 3-continued

| Sample | Time (min) | Acetone (wt %) |
|---|---|---|
| | 20 | 0.5 |
| | 30 | 0.31 |
| | 40 | 0.19 |
| | 50 | 0.13 |
| | 60 | 0.095 |
| | 90 | 0.042 |
| | 120 | 0.024 |
| Example 7 | 2 | 1.5 |
| | 10 | 1.0 |
| | 20 | 0.62 |
| | 30 | 0.41 |
| | 40 | 0.29 |
| | 50 | 0.24 |
| | 60 | 0.17 |
| | 90 | 0.12 |
| | 120 | 0.078 |
| | 180 | 0.034 |
| Example 8 | 2 | 1.5 |
| | 10 | 1.1 |
| | 20 | 0.52 |
| | 30 | 0.29 |
| | 40 | 0.17 |
| | 50 | 0.11 |
| | 60 | 0.071 |
| | 90 | 0.03 |
| | 120 | 0.016 |
| Example 9 | 2 | 0.98 |
| | 10 | 0.49 |
| | 20 | 0.29 |
| | 30 | 0.2 |
| | 40 | 0.13 |
| | 50 | 0.088 |
| | 60 | 0.078 |
| | 90 | 0.04 |
| | 120 | 0.024 |
| Example 10 | 2 | 1.5 |
| | 10 | 0.74 |
| | 20 | 0.39 |
| | 30 | 0.21 |
| | 40 | 0.13 |
| | 50 | 0.076 |
| | 60 | 0.05 |
| | 90 | 0.021 |

From the results in Table 3, the times required to dry the 10 samples of Dispersion 1 from 1.0 wt % to 0.1 wt % residual acetone were estimated, and are reported in Table 4, along with the initial concentration of residual acetone in the dispersion (measured at 2 minutes following the start of drying) and the operating conditions.

TABLE 4

| Example | Temp. (°C.) | Chamber Pressure (mbar) | Flow Rate of Stripping gas (SL/min) | Mixing Speed (rpm) | Initial Acetone Conc. (wt %) | Drying Time from 1.0 wt % to 0.1 wt % (hr) |
|---|---|---|---|---|---|---|
| 1 | 45 | 30 | 0.2 | 200 | 1.9 | 1.70 |
| 2 | 55 | 10 | 0.2 | 200 | 1.4 | 0.82 |
| 3 | 45 | 29 | 0.6 | 100 | 1.7 | 1.30 |
| 4 | 50 | 21 | 0.4 | 150 | 1.6 | 0.80 |
| 5 | 55 | 30 | 0.2 | 200 | 1.5 | 0.75 |
| 6 | 55 | 30 | 0.6 | 200 | 1.5 | 0.78 |
| 7 | 45 | 10 | 0.2 | 100 | 1.5 | 1.60 |
| 8 | 50 | 20 | 0.4 | 150 | 1.5 | 0.68 |
| 9 | 45 | 12 | 0.6 | 200 | 1.0 | 0.75 |
| 10 | 55 | 14 | 0.6 | 100 | 1.5 | 0.63 |

The data in Table 4 shows that temperature, pressure, and flow rate of stripping gas had large effects on drying time over the conditions studied. Mixing speed had little effect on the drying time for the range of conditions evaluated.

Controls 1-4

Another batch of Dispersion 1 was made in the same manner noted above, then dried using conventional drying technology comprising the use of a conventional Gruenberg single-pass convection tray-drier operating at 40° C. The dispersion was placed into the dryer and spread to four different depths to form Controls 1-4. A sample of dispersion was spread to a depth of 1 cm to form Control 1, 2 cm to form Control 2, 4 cm to form Control 3, and 5 cm to form Control 4. Samples of the dispersions dried in these tests were taken at various time intervals, and residual acetone was measured using headspace GC as previously described. The results are reported in Table 5.

TABLE 5

| Sample | Time (min) | Acetone (wt %) |
|---|---|---|
| Control 1 | 0 | 1.84 |
| | 15 | 0.84 |
| | 30 | 0.58 |
| | 60 | 0.24 |
| | 120 | 0.10 |
| | 240 | 0.02 |
| | 360 | 0.02 |
| Control 2 | 0 | 1.84 |
| | 15 | 1.34 |
| | 30 | 1.00 |
| | 60 | 0.60 |
| | 120 | 0.28 |
| | 240 | 0.10 |
| | 360 | 0.04 |
| Control 3 | 0 | 1.19 |
| | 15 | 1.10 |
| | 30 | 1.02 |
| | 60 | 1.03 |
| | 120 | 0.80 |
| | 240 | 0.52 |
| | 360 | 0.37 |
| Control 4 | 0 | 1.19 |
| | 15 | 1.15 |
| | 30 | 1.37 |
| | 60 | 1.45 |
| | 120 | 0.96 |
| | 240 | 0.65 |
| | 360 | 0.50 |

From the data in Table 5, the time to dry the dispersion from 1 wt % to 0.1 wt % was determined as a function of bed depth. These results are summarized in Table 6, and show that the time to dry the dispersion using conventional drying technology is much greater than that obtained with the process and apparatus of the present invention, as reflected in Examples 1-10. Indeed, for Controls 3 and 4, the concentration of residual acetone in the sample was greater than 0.1 wt % after 6 hours of drying in the tray-drier.

TABLE 6

| Control | Bed Depth (cm) | Initial Acetone Concentration (wt %) | Drying Time from 1.0 wt % to 0.1 wt % (hr) |
|---|---|---|---|
| 1 | 1 | 1.84 | 1.8 |
| 2 | 2 | 1.84 | 3.5 |
| 3 | 4 | 1.19 | >6 |
| 4 | 5 | 1.19 | >6 |

In Vitro Dissolution Test

A sample of the solid amorphous dispersion used in Example 4 was evaluated before and after secondary drying in an in vitro dissolution test to determine the effect of drying on concentration enhancement relative to the crystalline form of Drug 1. As a control, Control 5 consisted of crystalline Drug 1 alone. For this test, a sufficient amount of Dispersion 1 and Control 5 material was added to microcentrifuge test tubes so that the concentration of Drug 1 would have been 1000 μg/mL in both cases if all of the drug had dissolved. The test was performed in duplicate. The tubes were placed in a 37° C. temperature-controlled chamber, and 1.8 mL PBS at pH 6.5 and 290 mOsm/kg was added to each tube. The samples were mixed using a vortex mixer for about 60 seconds. The samples were centrifuged at 13,000 G at 37° C. for 1 minute. The resulting supernatant solution was then sampled and diluted 1:6 (by volume) with methanol and then analyzed by high performance liquid chromatography (HPLC). The contents of each tube were mixed on the vortex mixer and allowed to stand undisturbed at 37° C. until the next sample was taken. Samples were collected at 4, 10, 20, 40, 90, and 1200 minutes. The results are shown in Table 7.

TABLE 7

| Sample | Time (min) | Drug 1 Concentration (μg/mL) | AUC (min*μg/mL) |
|---|---|---|---|
| Example 4 (before secondary drying) | 0 | 0 | 0 |
| | 4 | 396 | 800 |
| | 10 | 760 | 4300 |
| | 20 | 814 | 12,100 |
| | 40 | 818 | 28,500 |
| | 90 | 767 | 68,100 |
| | 1200 | 323 | 672,800 |
| Example 4 (after secondary drying) | 0 | 0 | 0 |
| | 4 | 373 | 700 |
| | 10 | 746 | 4100 |
| | 20 | 818 | 11,900 |
| | 40 | 846 | 28,600 |
| | 90 | 780 | 69,200 |
| | 1200 | 314 | 676,400 |
| Control 5 (crystalline Drug 1) | 0 | 0 | 0 |
| | 4 | <1 | <2 |
| | 10 | <1 | <8 |
| | 20 | <1 | <18 |
| | 40 | <1 | <38 |
| | 90 | <1 | <88 |
| | 1200 | <1 | <1,200 |

The concentrations of drug obtained in these samples were used to determine the maximum concentration of drug ($MDC_{90}$) and the area under the concentration-versus-time curve ($AUC_{90}$) during the initial ninety minutes. The results are shown in Table 8.

TABLE 8

| Sample | $MDC_{90}$ (μg/mL) | $AUC_{90}$ (min*μg/mL) |
|---|---|---|
| Example 4 (before secondary drying) | 818 | 68,100 |
| Example 4 (after secondary drying) | 846 | 69,200 |
| Control 5 (crystalline Drug 1) | <1 | <88 |

The results in Table 8 show that the $MDC_{90}$ and $AUC_{90}$ of the spray-dried dispersion of Example 4 are about the same before and after secondary drying. The dispersion of Example 4 before secondary drying provided an $MDC_{90}$ that was greater than 818-fold that provided by crystalline drug (Control 5), and an $AUC_{90}$ that was greater than 774-fold that provided by crystalline drug. After secondary drying, the dispersion of Example 4 provided an $MDC_{90}$ that was greater than 846-fold that provided by crystalline drug, and an $AUC_{90}$ that was greater than 786-fold that provided by crystalline drug.

Dispersion 2

A placebo spray-dried dispersion (Dispersion 2) was formed by spray-drying HPMCAS using the following process. A spray solution was formed containing 12 wt % HPMCAS (AQOAT-MF) and 88 wt % acetone. The solution was pumped using a Soavi 3-head piston pump to a Niro Model 12.5 spray-dryer equipped with a pressure nozzle (Delavan SDXIII SD-69 90° cone face). The solution was pumped to the spray-dryer at a rate of about 375 kg/hr, with an atomization pressure of 150 bar. Nitrogen drying gas entered the drying chamber at an inlet temperature of 180° C. and a flow rate of 1250 kg/hr. The evaporated solvent and drying gas exited the spray-dryer at an outlet temperature of 46° C. The so-formed dispersion powder was collected in a cyclone. The properties of the placebo spray-dried dispersion very closely mimicked those of drug-containing Dispersion 1, and are reported in Table 9.

TABLE 9

| Bulk Properties (Before Secondary Drying) | Value |
|---|---|
| Bulk Specific Volume (mL/g) | 5.6 |
| Tapped Specific Volume (mL/g) | 4.3 |
| Mean Particle Diameter (μm) | 65 |

Example 11

Dispersion 2 was subjected to secondary drying by charging a 50-L capacity Ekato VPT agitated bed vacuum dryer, having an agitator diameter of 0.6 m, and modified to have a stripping gas inlet port with 11 kg of the placebo dispersion. The dryer was operated at a jacket temperature of 50° C., a pressure of 20 mbar, a stir rate speed of 94 rpm, and a nitrogen stripping gas flow of 10.7 SL/min (or 0.97 SL/min-kg).

Residual acetone was measured using headspace GC as previously described. The results are reported in Table 10. The drying time required to reach 0.1 wt % residual acetone at the 50-L scale was about 1.6 hours.

TABLE 10

| Time (min) | Acetone (wt %) |
|---|---|
| 0 | 2.10 |
| 15 | 0.98 |
| 30 | 0.63 |
| 45 | 0.38 |
| 60 | 0.24 |
| 90 | 0.11 |
| 120 | 0.05 |
| 150 | 0.03 |
| 180 | 0.02 |
| 210 | <0.02 |
| 240 | <0.02 |

Examples 12-16

Dispersion 2 was dried and residual acetone content measured as in Example 11, but varying the drying conditions as noted in Table 11. Example 11 operating conditions are included for comparison. The results are reported in Table 12.

TABLE 11

| Sample | Jacket Temp. (° C.) | Chamber Pressure (mbar) | Flow rate of Nitrogen Stripping gas SL/min | Flow rate of Nitrogen Stripping gas SL/min-kg | Charge to dryer (kg) | Mixing Speed (rpm) | Mixing Velocity (m/sec)* | Froude Number |
|---|---|---|---|---|---|---|---|---|
| Example 11 | 50 | 20 | 10.7 | 11 | 0.97 | 94 | 3 | 1.5 |
| Example 12 | 40 | 40 | 53.3 | 11 | 4.85 | 10 | 0.3 | 0.01 |
| Example 13 | 40 | 40 | 53.3 | 11 | 4.85 | 94 | 3 | 1.5 |
| Example 14 | 40 | 40 | 26.7 | 5.5 | 4.85 | 94 | 3 | 1.5 |
| Example 15 | 50 | 20 | 53.3 | 11 | 4.85 | 94 | 3 | 1.5 |
| Example 16 | 50 | 20 | 21.3 | 11 | 1.94 | 94 | 3 | 1.5 |

*Mixing velocity = $\pi DN$, where D = 0.6 m and N = mixing speed (in rev/sec)

TABLE 12

| Example | Time (min) | Acetone (wt %) |
|---|---|---|
| 12 | 0 | 2.06 |
|  | 15 | 1.32 |
|  | 30 | 1.26 |
|  | 45 | 0.87 |
|  | 60 | 0.61 |
|  | 90 | 0.49 |
|  | 120 | 0.35 |
|  | 150 | 0.18 |
|  | 180 | 0.19 |
|  | 210 | 0.10 |
|  | 240 | 0.15 |
| 13 | 0 | 2.74 |
|  | 15 | 1.16 |
|  | 30 | 0.90 |
|  | 45 | 0.57 |
|  | 60 | 0.39 |
|  | 90 | 0.29 |
|  | 120 | 0.25 |
|  | 150 | 0.11 |
|  | 180 | 0.17 |
|  | 210 | 0.10 |
|  | 240 | 0.05 |
| 14 | 0 | 3.07 |
|  | 15 | 1.68 |
|  | 30 | 0.91 |
|  | 45 | 0.56 |
|  | 60 | 0.39 |
|  | 90 | 0.24 |
|  | 120 | 0.15 |
|  | 150 | 0.13 |
|  | 180 | 0.07 |
|  | 210 | 0.08 |
|  | 240 | 0.07 |
| 15 | 0 | 2.90 |
|  | 15 | 0.88 |
|  | 30 | 0.38 |
|  | 45 | 0.25 |
|  | 60 | 0.17 |
|  | 90 | 0.07 |
|  | 120 | 0.04 |
|  | 150 | 0.04 |
|  | 180 | 0.05 |
|  | 210 | 0.04 |
|  | 240 | 0.04 |
| 16 | 0 | 4.77 |
|  | 15 | 1.15 |
|  | 30 | 0.62 |
|  | 45 | 0.32 |
|  | 60 | 0.21 |
|  | 90 | 0.10 |
|  | 120 | 0.06 |
|  | 150 | 0.03 |
|  | 180 | 0.02 |
|  | 210 | <0.02 |
|  | 240 | <0.02 |

From the results in Table 12, the approximate drying times to reach 0.1 wt % residual acetone were determined for Examples 12-16 and are shown in Table 13. Example 11 drying time is included for comparison.

TABLE 13

| Example | Approximate Drying Time (hr) |
|---|---|
| 11 | 1.6 |
| 12 | 3.5 |
| 13 | 2.5 |
| 14 | 3.0 |
| 15 | 1.3 |
| 16 | 1.5 |

Example 17

135 kg of Dispersion 2 were dried in a 1000-L capacity Ekato VPT having an agitator diameter of 1.3 m, and modified to have a stripping gas inlet port. The drier was operated with a jacket temperature of 50° C., a chamber pressure of 20 mbar, a mixing velocity of 3 m/sec (44 rpm, corresponding to a Froude Number of 0.7), and a nitrogen stripping gas flow rate of 56 SL/min (0.41 SL/min-kg).

The concentration of residual acetone in Dispersion 2 was measured as a function of time using headspace GC analysis as previously described. The results are reported in Table 14.

TABLE 14

| Time (min) | Acetone (wt %) |
|---|---|
| 0 | 2.4 |
| 10 | 1.8 |
| 26 | 1.2 |
| 40 | 0.79 |
| 55 | 0.53 |
| 70 | 0.37 |
| 85 | 0.25 |
| 100 | 0.18 |
| 115 | 0.13 |
| 130 | 0.10 |
| 145 | 0.076 |
| 160 | 0.057 |
| 175 | 0.044 |

The time required to dry the placebo dispersion from 1.0 wt % to 0.1% residual acetone at the 1000-L scale was about 1.6 hrs.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

The invention claimed is:

1. A process for producing a pharmaceutical composition, comprising the steps:

(a) forming a solution comprising a drug, an excipient and a solvent;
(b) in a spray drying apparatus, atomizing said solution into droplets and removing at least a portion of said solvent from said droplets so as to form at least partially non-crystalline drug-containing particles containing less than about 10 wt % of said solvent; and
(c) conducting a secondary drying of said drug-containing particles of step (b) by
  (i) removing the drug-containing particles from the spray drying apparatus and introducing said drug-containing particles of step (b) into a secondary drying apparatus having an external wall, the secondary drying apparatus being a separate chamber from the spray drying apparatus;
  (ii) circulating said drug-containing particles within said secondary drying apparatus by means of a mechanical agitator independent of said wall;
  (iii) flowing a stripping gas through said secondary drying apparatus while reducing a total pressure to and maintaining the total pressure, within said secondary drying apparatus at less than about 0.75 atm;
  (iv) conducting the secondary drying step for about 30 minutes to about 20 hours to remove solvent from the drug-containing particles such that the drug-containing particles contain less than about 0.5 wt % of the solvent; and
  (v) removing said stripping gas and at least a portion of said solvent from said secondary drying apparatus.

2. The process of claim 1 wherein step (c)(iii) further comprises forming a bed of said drug-containing particles and flowing said stripping gas through said bed.

3. The process of claim 2 wherein said drug-containing particles in said secondary drying apparatus are in a bed having an average depth of at least 10 cm.

4. The process of claim 1 wherein the secondary drying step is conducted for about 30 minutes to about 2 hours.

5. The process of claim 4 wherein said drug-containing particles are in the form of a solid amorphous dispersion.

6. The process of claim 1 wherein the amount of solvent remaining in said drug-containing particles after said process is less than about 0.1 wt % of the total mass of said particles.

7. The process of claim 1 wherein the secondary drying step is conducted for about 30 minutes to about 4 hours.

8. The process of claim 1 wherein said total pressure in said secondary drying apparatus is less than about 0.1 atm.

9. The process of claim 1 wherein said stripping gas has a flow rate of at least about 0.2 standard liters per minute per kilogram of particles to be dried.

10. The process of claim 1 wherein said drug is a cholesteryl ester transfer protein inhibitor selected from the group consisting of [2R,4S]-4-[acetyl-(3,5-bis-trifluoromethyl-benzyl)-amino]-2-ethyl-6-trifluoromethyl-3,4dihydro-2H-quinoline-1-carboxylic acid isopropyl ester, [2R,4S]4-[(3,5-bis-trifluoromethyl-benzyl)-methoxycarbonylamino]-2-ethyl-6-trifluoromethyl-3,4-dihydro-2H-quinoline-1-carboxylic acid ethyl ester, [2R,4S]4-[(3,5-bistrifluoromethylbenzyl)-methoxycarbonyl-amino]-2-ethyl-6-trifluoromethyl-3,4-dihydro-2H-quinoline-1-carboxylic acid isopropyl ester, (2R)-3-[[3-(4-chloro-3-ethylphenoxy)phenyl][[3-(1,1,2,2-tetrafluoroethoxy)phenyl]methyl]amino]-1,1,1-trifluoro-2-propanol, and (2R,4R,4aS)-4-[amino-(3,5-bis-(trifluoromethyl-phenyl)-methyl]-2-ethyl-6-(trifluoromethyl)-3,4-dihydroquinoline-1-carboxylic acid isopropyl ester, S-[2-([[1-(2-ethylbutyl)cyclohexyl]carbonyl]amino)phenyl]2-methylpropanethioate.

* * * * *